United States Patent
King et al.

(10) Patent No.: US 11,668,633 B2
(45) Date of Patent: Jun. 6, 2023

(54) COMPRESSIVE CREEP FLOW DETERMINATION IN FLUIDS

(71) Applicant: THE BOEING COMPANY, Chicago, IL (US)

(72) Inventors: Garnel King, Madison, AL (US); Dennis L. Coad, Madison, AL (US); Jennifer L. Chevallier, Huntsville, AL (US)

(73) Assignee: The Boeing Company, Arlington, VA (US)

( * ) Notice: Subject to any disclaimer, the term of this patent is extended or adjusted under 35 U.S.C. 154(b) by 631 days.

(21) Appl. No.: 16/854,537

(22) Filed: Apr. 21, 2020

(65) Prior Publication Data

US 2021/0325286 A1   Oct. 21, 2021

(51) Int. Cl.
*G01N 3/14* (2006.01)
*G01N 3/04* (2006.01)

(52) U.S. Cl.
CPC ............... *G01N 3/14* (2013.01); *G01N 3/04* (2013.01); *G01N 2203/0019* (2013.01); *G01N 2203/0071* (2013.01); *G01N 2203/0242* (2013.01); *G01N 2203/0617* (2013.01)

(58) Field of Classification Search
CPC ..... G01L 3/14; G01L 3/04; G01L 3/12; G01L 3/02; G01N 2203/0071; G01N 2203/0242; G01N 2203/0617; G01N 2203/0019; G01N 2203/0033; G01N 33/442
See application file for complete search history.

(56) References Cited

U.S. PATENT DOCUMENTS 8,789,425 B2   7/2014   Oh et al.

FOREIGN PATENT DOCUMENTS

| CN | 203350129 U | | 12/2013 | |
| CN | 105674932 A | * | 6/2016 | |
| CN | 107843502 A | | 3/2018 | |
| CN | 108051307 A | * | 5/2018 | ........... G01N 15/082 |
| CN | 109238851 A | * | 1/2019 | |
| CN | 110132741 A | | 8/2019 | |
| GB | 1159952 A | | 7/1969 | |
| KR | 101178448 B1 | * | 9/2012 | |
| WO | 2012051647 A1 | | 4/2012 | |

OTHER PUBLICATIONS

Extended European Search Report for Application 21160533.2, pp. 1-8, dated Jun. 8, 2021.

* cited by examiner

*Primary Examiner* — Jonathan M Dunlap
(74) *Attorney, Agent, or Firm* — Patterson + Sheridan, LLP (57) ABSTRACT

The present disclosure provides an apparatus and method of use thereof for compressive creep testing of materials in the presence of fluids. The apparatus includes a cantilever arm connected on a first end to a cantilever pivot and including a weight holder on a second end; a first platen connected to the cantilever arm via a swivel located between the first end and the second end; a reservoir; and a second platen disposed within the reservoir and positioned to secure a sample between the first platen and the second platen when a force is applied via the weight holder and the first platen to a sample. Electrical properties of the material can be monitored and measured during the compression creep testing.

20 Claims, 9 Drawing Sheets

COMPRESSIVE CREEP FLOW DETERMINATION IN FLUIDS

STATEMENT OF GOVERNMENT INTEREST

This invention was made with government support under contract NAS15-10000 awarded by the National Aeronautics and Space Administration (NASA). The government has certain rights in the invention.

FIELD

Aspects of the present disclosure relate to systems and methods for performing compression creep testing on materials.

BACKGROUND

Various material properties can only be determined reliably after lengthy testing. Such tests may take days, months, or years, which requires great consistency in the test environment and test apparatus over that length of time to yield reliable measurements. The measurements can be particularly complicated when testing the interactions between two materials or the effects of one material on another.

The present disclosure provides for an apparatus in one aspect, the apparatus comprising: a cantilever arm connected on a first end to a cantilever pivot and including a weight holder on a second end; a first platen connected to the cantilever arm via a swivel located between the first end and the second end; a reservoir; and a second platen disposed within the reservoir and positioned to secure a sample between the first platen and the second platen when a force is applied via the weight holder and the first platen to a sample.

In one aspect, in combination with any example apparatus above or below, the apparatus further comprises: a compression interlock configured to position the second end of the cantilever arm at one of a first height and a second height, wherein: at the first height the first platen is positioned to transfer the force applied via the weight holder to a sample positioned on the second platen, and at the second height the first platen is positioned to not transfer the force applied via the weight holder to a sample positioned on the second platen.

In one aspect, in combination with any example apparatus above or below, the first platen and the second platen respectively define a first flat surface and a second flat surface configured to contact a sample of a smaller cross-sectional area than the first platen or the second platen.

In one aspect, in combination with any example apparatus above or below, at least one of the first platen or the second platen includes an expansion gauge.

In one aspect, in combination with any example apparatus above or below, the reservoir further comprises: a fluid basin in which the second platen is disposed, wherein the fluid basin extends to a first height greater than a height of a sample held between the first platen and the second platen; a fluid inlet disposed at a second height at or above the first height, wherein the fluid inlet is configured to configured to allow fluid to flow into the fluid basin; and a fluid outlet disposed at a third height at or above the first height and at or below the second height, wherein the fluid outlet is configured to allow fluid to flow out of the fluid basin.

In one aspect, in combination with any example apparatus above or below, the swivel is configured to keep the first platen in contact with a sample held between the first platen and the second platen as the sample deforms under the force applied via the weight holder and the first platen.

In one aspect, in combination with any example apparatus above or below, the apparatus further comprises: an electrical meter defined in the reservoir, configured to measure an electrical aspect of the sample held between the first platen and the second platen while the first platen is electrically isolated from the second platen.

The present disclosure provides for a device in one aspect, the device, comprising: a reservoir including a fluid basin in which a first platen, a sample positioned on the first platen, and a fluid rising to a fluid level above an upper surface of the sample are included; a cantilever including: a mount mounted to a surface on which the reservoir is disposed and including a pivot; a cantilever arm connected on a first end to the pivot including a weight holder on a second end opposite to the first end and including a swivel between the first end and the second end; and a second platen connected to the swivel and held in contact with the upper surface of the sample via a downward force applied on the second end to transfer a compressive load to the sample.

In one aspect, in combination with any example device above or below, the fluid is one of deionized water, jet fuel, and hydraulic fluid.

In one aspect, in combination with any example device above or below, the sample is made of a polymer material with a lower hardness than the first platen and the second platen.

In one aspect, in combination with any example device above or below, the device further comprises an electrical meter disposed in the reservoir and configured to measure an electrical aspect across the sample.

In one aspect, in combination with any example device above or below, the device further comprises a fluid level sensor configured to generate an alert when a fluid level is at or below the upper surface of the sample.

In one aspect, in combination with any example device above or below, the wherein the reservoir further comprises: a fluid inlet configured to deposit fluid into the reservoir; and a fluid outlet configured to remove fluid from the reservoir, wherein the fluid outlet is disposed at an outlet height above the upper surface of the sample.

In one aspect, in combination with any example device above or below, the device further comprises a test chamber configured to control a temperature of an environment in which the reservoir is disposed.

In one aspect, in combination with any example device above or below, the weight holder comprises a dowel configured to receive and hold in position one or more weights of one or more predefined weights.

In one aspect, in combination with any example device above or below, the one or more weights held by the weight holder are selected based on a length of the cantilever arm, a distance between the pivot and the second end, and a desired level of the compressive load to apply.

The present disclosure provides a method in one aspect, the method, comprising: placing a sample of a given material between a first platen and a second platen, wherein: a cross-sectional area of the first platen and a cross-sectional area of the second platen is greater than a cross-sectional area of the sample, and the sample is a disposed in a reservoir; filling the reservoir with a fluid to submerge the sample within the reservoir; applying a load to a cantilever arm connected to the first platen to impart a compressive force between the first platen and the second platen to the sample; in response to a predefined length of time passing, measuring a second height and a second cross-sectional area of the sample; and indicating a creep rate of the given material in presence of the fluid.

In one aspect, in combination with any example method above or below, the method further comprises: measuring a force between the cantilever arm and the first platen.

In one aspect, in combination with any example method above or below, the method further comprises: monitoring a level of the fluid over the predefined length of time; and in response to the level of the fluid dropping to a predefined level, adding additional fluid to the reservoir to keep the sample submerged.

In one aspect, in combination with any example method above or below, the method further comprises: measuring an electrical aspect of the sample between the first platen and the second platen.

BRIEF DESCRIPTION OF THE DRAWINGS

So that the manner in which the above recited features can be understood in detail, a more particular description, briefly summarized above, may be had by reference to example aspects, some of which are illustrated in the appended drawings.

DETAILED DESCRIPTION

The present disclosure provides for a testing apparatus configured to provide a consistent test environment for measuring a creep rate (also referred to as cold flow) of a material by applying a constant static compressive load to a sample of the material to be measured. In various aspects, the sample is held in a reservoir containing a fluid and the sample is compressed between two platens through which a known compressive force is evenly and consistently applied to a sample over the course of the test. The reservoir maintains a fluid level that keeps the sample submerged in the fluid, and the testing apparatus is maintained in a chamber or other environment having a controlled temperature and humidity. The fluid may be circulated and/or replaced over time. Further, an electrical potential may be applied across the sample to detect creep rates in the presence of the fluid and/or an electrical current.

Figure 1A:
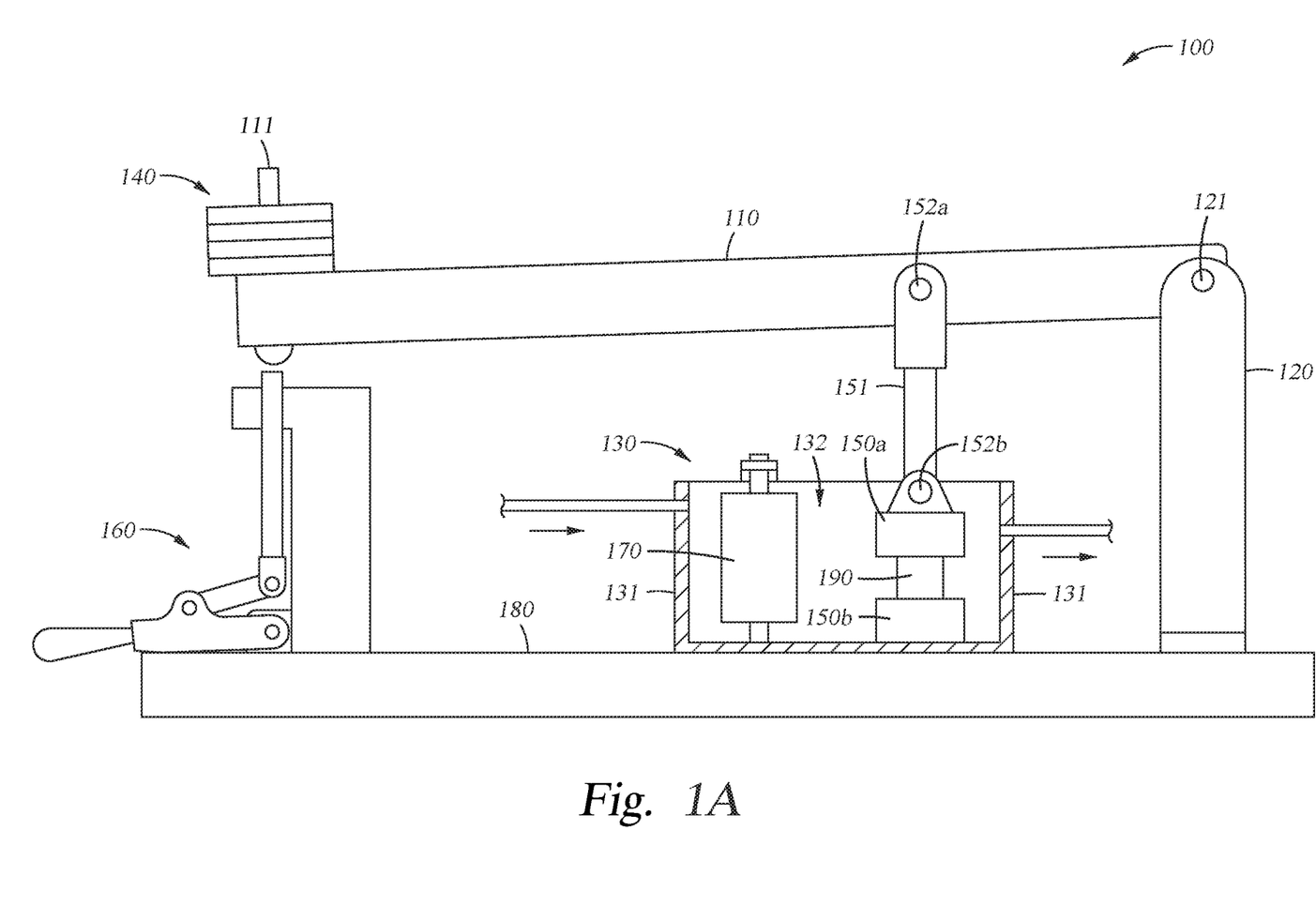
FIG. 1A is a side view of a creep test fixture applying load to a sample, according to aspects of the present disclosure.
Figure 1B:
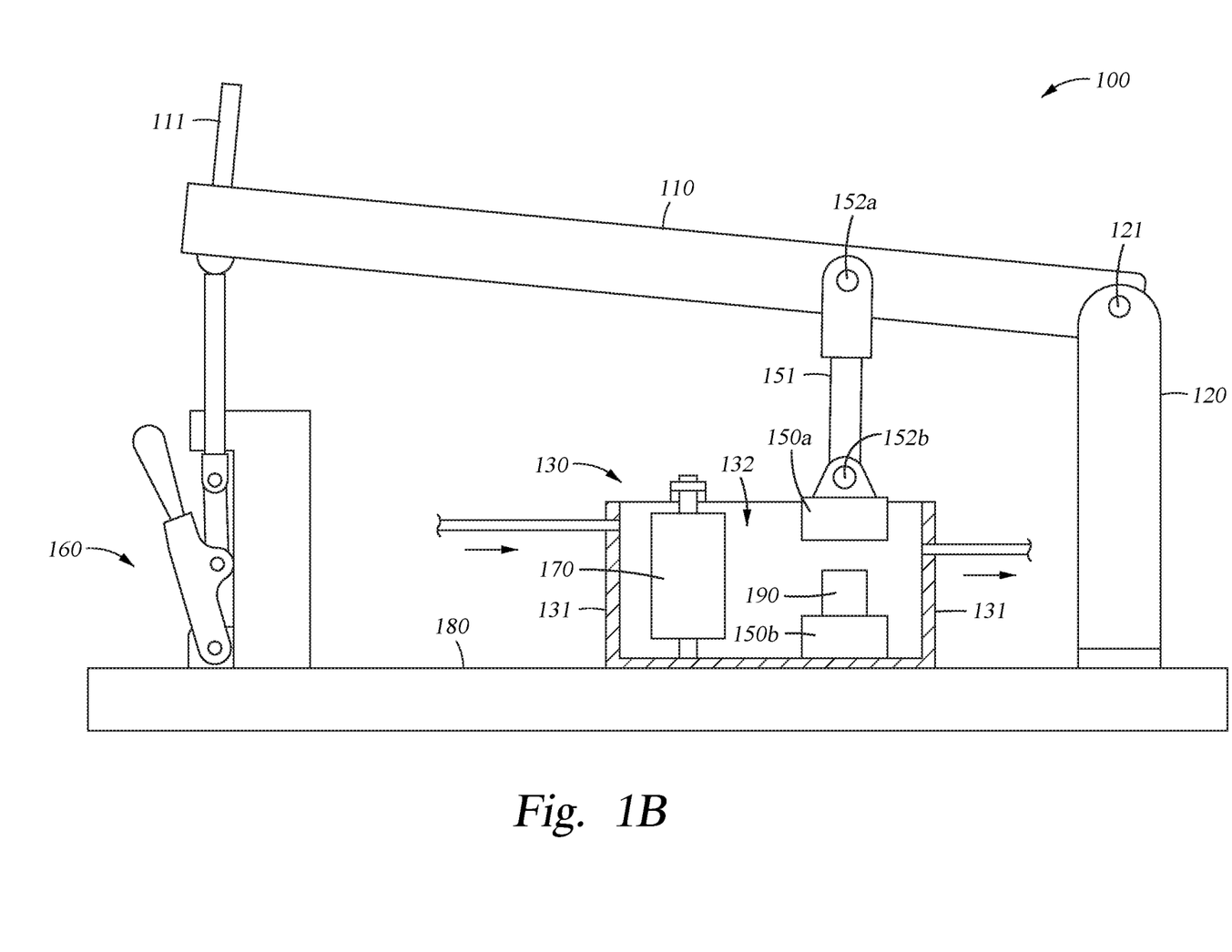
FIG. 1B is side view of a creep test fixture not applying load to a sample, according to aspects of the present disclosure.

FIGS. 1A and 1B are side views of an aspect of a creep test fixture 100 applying load (per FIG. 1A) and not applying load (per FIG. 1B), according to aspects of the present disclosure. In this aspect, the creep test fixture 100 includes a cantilever arm 110, a cantilever pivot 121 included in a mount 120, a reservoir 130, one or more weights 140 that are selectively added/removed from the creep test fixture 100, a first platen 150a, and a second platen 150b (collectively platens 150). The creep test fixture 100 optionally includes, in some aspects, one or more of a compression interlock 160, a reservoir fluid level sensor 170, and a base 180.

Also illustrated is a sample 190, positioned between the platens 150. In various aspects, the sample 190 is defined as a material of a given size and shape based on the size and shape of the platens 150 and the distance between the platens 150, but may also be defined based on a grain direction in the material (e.g., parallel, perpendicular, or at another predefined angle relative to the direction of the compressive force to be applied to the sample 190).

In FIG. 1A, the weights 140 are held on the weight holder 111 and the compression interlock 160 is disengaged, thus allowing the force of gravity and the leverage of the cantilever arm 110 relative to the pivots 121, 152 to apply a compressive force through the platens 150 to the sample 190.

In FIG. 1B, an operator has removed (or not yet added) the weights 140 to the weight holder 111 and the compression interlock 160 is engaged, thus preventing the platen 150a from applying a compressive force to the sample 190 by holding the cantilever arm 110 (and thereby the first platen 150a) away from the sample 190.

Further in FIGS. 1A and 1B, the reservoir 130 is depicted without fluid so as to not distract from the components of the creep test fixture 100 and the positioning of the sample 190. In various aspects, the creep test fixture 100 may be used without a fluid in the reservoir 130.

In aspects that include a base 180, the mount 120 and the reservoir 130 can be mounted to the base 180, which provides a shared point of reference for the heights of the elements included in or connected thereto. The base 180 can be mounted to a platform (e.g., a table, workbench, test stand). In various aspects, the base 180 is mounted to the platform in parallel to the horizon to ensure that the creep test fixture 100 applies a compressive force to the sample 190 that is substantially vertical (i.e., aligned with gravity). In other aspects, the base 180 can be mounted to a platform at a predefined offset to the horizon to ensure that the creep test fixture 100 applies a compressive force to the sample 190 with a shear component or so that a fluid held in the reservoir 130 flows in a given direction out of the reservoir 130. In aspects that do not include a base 180, the mount 120 and the reservoir 130 (and if included, the compression interlock 160) can be mounted to separate platforms with the same or different heights and alignments relative to the horizon.

The cantilever arm 110 is connected on a first end to the cantilever pivot 121 of the mount 120, about which the cantilever arm 110 can rotate or swing. The mount 120 is provided to position the cantilever pivot 121 (and thereby the first end of the cantilever arm 110) at a known height and position relative to the reservoir 130 to align the platens 150 for compressing the sample 190. The cantilever arm 110 includes a weight holder 111 on a second end distal to the cantilever pivot 121 that is configured to hold one or more weights 140 of various sizes/weights. In some aspects, the weight holder 111 is a dowel, and the weights 140 include through-holes that the dowel is inserted through to capture one or more of the weights 140 on the second end of the cantilever arm 110. In other aspects, the weight holder 111 may include magnetic fasteners, screw/bolt fasteners, cupped holders, horizontal bars, etc. to receive a user-selected number and type of weights 140 for use during creep testing. An operator is therefore able to adjust the amount of compressive force to apply to the sample 190 depending on the amount of weight held by the weight holder 111, the length of the cantilever arm 110, and the relative distances between the cantilever pivot 121 and the connection point with the first platen 150a.

The weights 140 may include various components of a known weight of various shapes and sizes. In the illustrated aspects, the weights 140 are provided with two flat surfaces opposing one another to allow multiple weights 140 to be stacked together. Additionally, the weights 140 are illustrated as including a through-hole to allow the weights 140 to be secured to the weight holder 111 and to be aligned with one another when installed. In various aspects, two or more weights 140 are provided at different known masses/weights (i.e., X kg and Y kg, where X≠Y) to allow an operator to select a desired total mass/weight (e.g., X+Y kg) to install on the cantilever arm 110 to impart a desired force on the sample 190 for the duration of creep testing. The terms mass and weight can be used interchangeably herein to refer to a known quality of the weights 140 to provide a known quantity of compressive force when installed in the creep test fixture 100 (e.g., a weight 140 of X kg provides a downward force of Y Newtons (N), but X kg may be referred to as either of the 'weight' or 'mass' of the weight 140).

In aspects that include a compression interlock 160, depending on whether the compression interlock 160 is disengaged (per FIG. 1A) or engaged (per FIG. 1B), the cantilever arm 110 is respectively permitted to or prevented from swinging downward to apply compressive force to a sample 190 between the platens 150. For example, when the compression interlock 160 is engaged, the compression interlock 160 is fixed in place so that the first platen 150a is blocked from coming within a predefined distance of the second platen 150b (e.g., defining a gap between the platens 150). In contrast, when the compression interlock 160 is disengaged, the first platen 150a can contact the second platen 150b (or compress a sample 190 held therebetween). In aspects that exclude a compression interlock 160, an operator may position a temporary interlock under the cantilever arm 110 to load weights 140 onto the weight holder 111 or may otherwise hold the cantilever arm 110 so that the compressive force is not applied to the sample 190 through the platens 150 until creep testing is ready to begin.

Figure 2A:
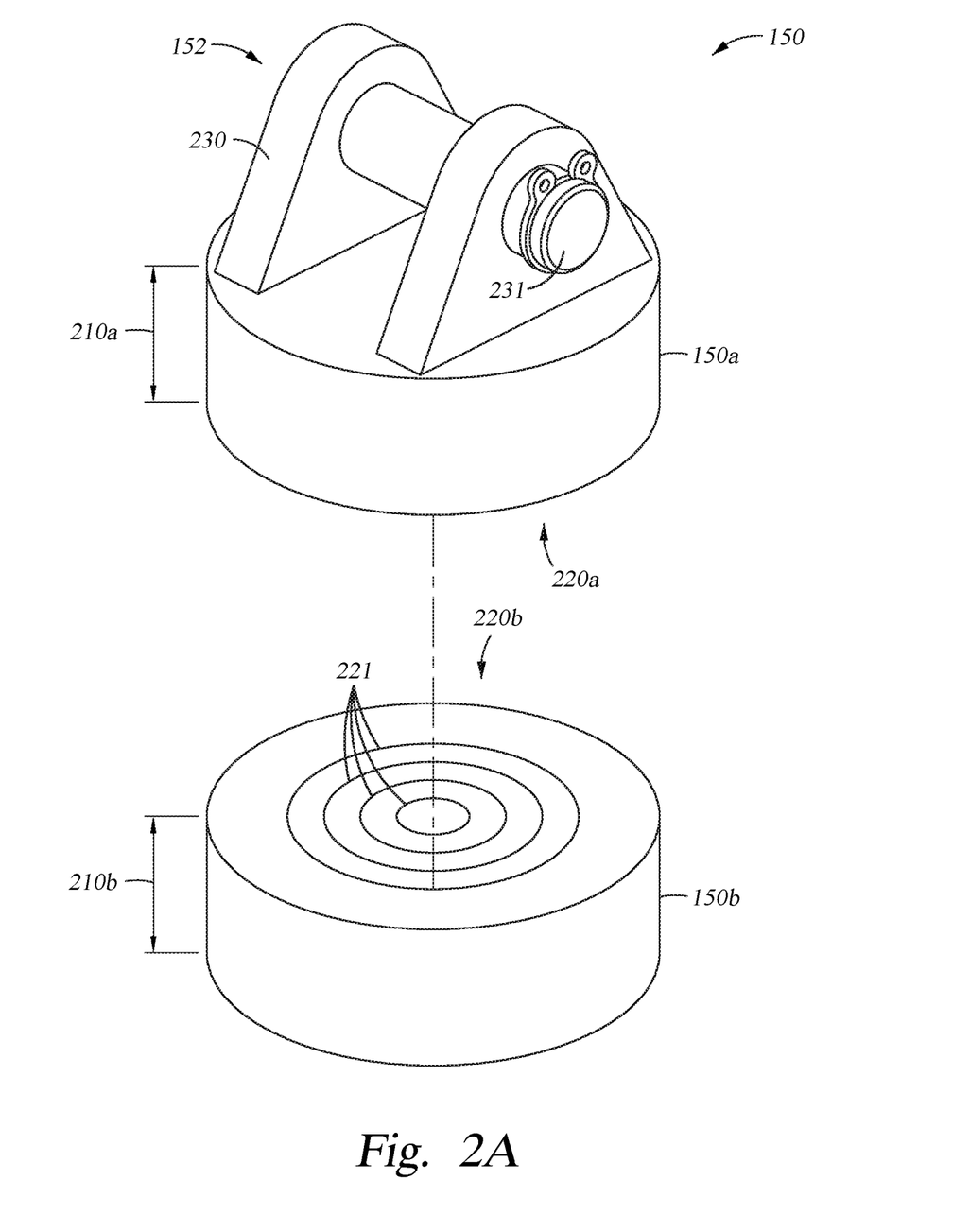
FIG. 2A-2D illustrates detailed views of the platens, according to aspects of the present disclosure.

The first platen 150a (also referred to as an upper platen or a mobile platen) is connected to the cantilever arm 110 via a platen arm 151 having a first swivel or pivot joint 152a (generally pivot joint 152) located medially along the length of the cantilever arm 110 (i.e., between the first end and the second end). In some aspects, the platen arm 151 is an extension of the first platen 150a. In other aspects, the platen arm 151 is a separate component from the first platen 150a and is connected to the first platen 150a by a second swivel or pivot joint 152b. In some aspects, the platen arm 151 includes a force meter configured to measure a force between the cantilever arm 110 and the first platen 150a to allow for calibration of the force applied to the sample 190 along with providing a start time of load for quick acting samples 190 undergoing creep test. When the cantilever arm 110 is raised or lowered, the first platen 150a counter-rotates about the pivot joint(s) 152 so that a contacting surface of the first platen 150a remains in a consistent (generally) parallel plane with a contacting surface of the second platen 150b. Also the first platen 150a has a self-aligning feature that allows the first platen 150a to align the planes of the first and second platens 150a, 150b. The second platen 150b (also referred to as a lower platen or a fixed platen) is disposed within the reservoir 130 and is positioned and aligned with the first platen 150a so that the platens 150 can secure the sample therebetween when the cantilever arm 110 is permitted (e.g., by the compression interlock 160) to apply a downward force through the platens 150. The platens 150 are discussed in greater detail in regard to FIG. 2.

The reservoir 130 includes one or more walls 131 that define a fluid basin 132 in which the platens 150 and secured sample 190 are held during creep testing. Although illustrated as generally rectangular in cross-section in the Figures, the reservoir 130 can also be provided with any number of different cross-sectional shapes including, but not limited to: circular, ovular, triangular, pentagonal, other polygonal shapes as well as other irregular shapes. The reservoir 130 is discussed in greater detail in regard to FIG. 3.

In some aspects, a fluid level sensor 170 is provided in the reservoir 130 to signal when the fluid in the reservoir 130 deviates from the desired fluid level. The fluid level sensor 170 includes electronic sensors as well as physical sensors or indicators, such as a bobbin or a float connected to a control lever that rises and falls in accordance with the fluid level in the reservoir 130. In some aspects, when the fluid drops to or below the upper surface of the sample 190, the fluid level sensor 170 generates an alert that signals the fluid source to provide additional fluid to the reservoir 130 and/or indicates to a test operator that the fluid level has dropped. In some aspects, when the fluid rises above a predefined fluid level, the fluid level sensor 170 operates or engages a fluid outlet to drain excess fluid from the reservoir 130 (e.g., to prevent overflow).

In some aspects, an electrical meter 175 (illustrated in FIG. 2D) is connected to the first platen 150a and the second platen 150b to measure an electrical aspect of the sample 190. In some aspects, the sample 190 isolates the platens 150 from one another, while in other aspects, a coating, such as, for example, a Diamond Like Coating (DLC) that provides lubrication for self-alignment and electrical resistance, on the surfaces of one or more of the platens 150 provide electrical isolation. In some aspects, the electrical meter 175 is a multimeter or specific meter (e.g., ohm meter, voltmeter) designed to measure one or more of: resistance, conductivity, impedance, voltage breakdown, etc., in alternating current (AC) (including at radio frequencies) or direct current (DC) scenarios. The electrical meter 175 is configured to account for the sample 190 being fully or partially submerged in a fluid, and the effects of the fluid on the measured electrical aspect. The electrical meter 175 measures the values of the electrical aspect(s) over time to determine the effects of the fluid and creep on the material of the sample 190.

Although not illustrated, the creep test fixture 100 can be placed in a test chamber, either alone or with other creep test fixtures 100 and associated control and measurement hardware. The test chamber provides a controlled environment for performing creep testing, which can include a controller temperature and/or atmosphere (e.g., one or more of a predefined pressure and gas/atmosphere composition). In some aspects, the control and measurement hardware includes fluid tanks, piping, and pumps to fill the fluid reservoirs 130 with a designated fluid to a designed fluid level and to maintain that fluid level. The test chamber can also include various temperature control devices (e.g., heaters, chillers, air conditioning) to maintain a desired temperature in the atmosphere and/or the fluid. Additionally, the test chamber can include an electrical supply to power the control and measurement hardware, lights, the electrical meter 175, etc.

Figure 1C:
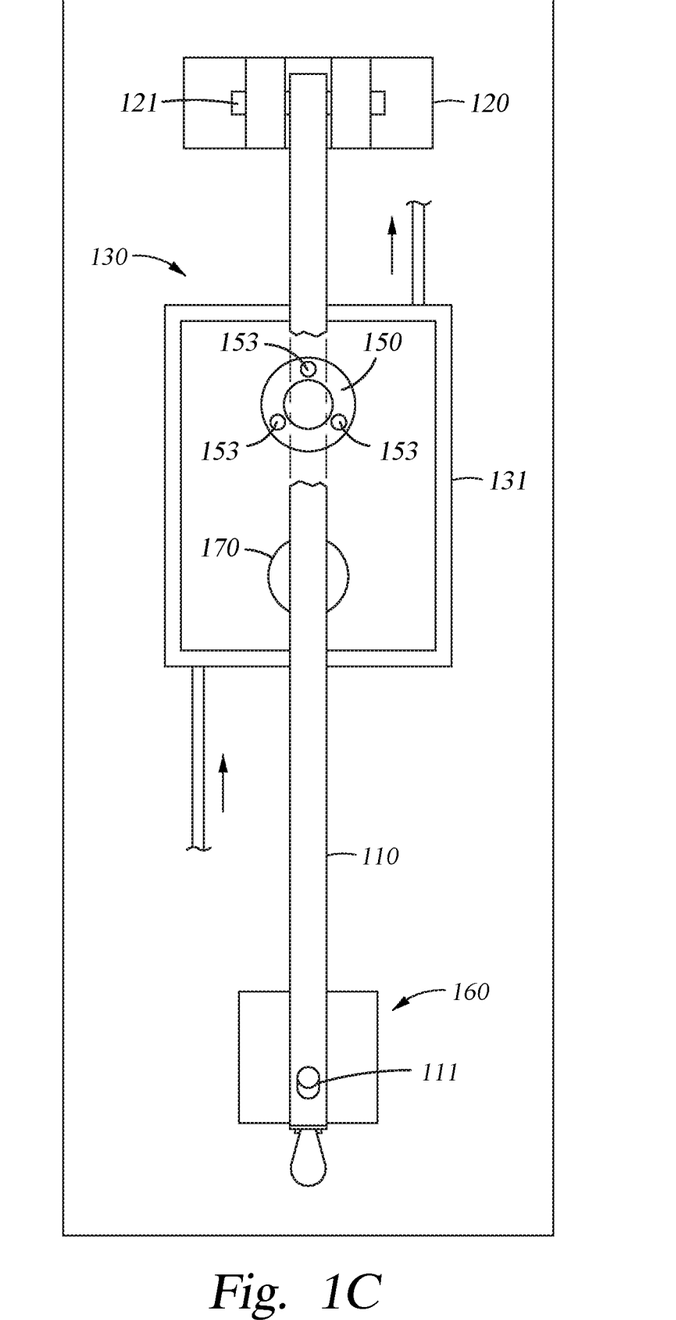
FIG. 1C is a top view of a creep test fixture, according to aspects of the present disclosure.

FIG. 1C is a top view of a creep test fixture 100, according to aspects of the present disclosure. FIG. 1C illustrates a plurality of sensors 153 connected with the platens 150 and disposed around the sample 190. In some aspects, the sensors 153 may be mounted with the upper platen 150a or the cantilever arm 110 and contact the lower platen 150b to measure travel of the upper platen 150a relative to the lower platen 150b as the sample 190 deforms. In some aspects, the sensors 153 may be mounted with the lower platen 150b or the reservoir 130 and contact the upper platen 150a to measure travel of the upper platen 150a relative to the lower platen 150b as the sample 190 deforms. The sensors 153 may be disposed at regular or irregular intervals around the sample 190, and more or fewer than the three sensors 153 illustrated in FIG. 1C may be used in various aspects. In some aspects, the sensors 153 are Linear Variable Differential Transducers (LVDT), but other distance gauges (e.g., range finders, rulers) may be used in various aspects in combination with or instead of LVDT sensors.

FIG. 2A illustrates detailed views of the platens 150 having flat surfaces to engage the sample 190, according to aspects of the present disclosure. The platen 150 is made of a material that is harder than that of the sample 190 to be tested, and may be provided with various thicknesses 210a,b to set a face 220a,b of the platen 150a,b at various heights relative to the reservoir 130. For example, the sample 190 can be a polymer material (e.g., NAFION®, available from The Chemours Company of Wilmington, Del.) of a lower hardness than the material of the platens 150 (e.g., a steel, tungsten, titanium). In another example, a lower platen 150b may be provided at a thickness 210b of X cm or of Y cm to extend upward from a floor of the reservoir 130 to different heights. Similarly, an upper platen 150a may be provided at a thickness 210a of X cm or of Y cm to extend into the reservoir 130 to different depths. Additionally or alternatively, the length of the platen arm 151 can be provided at different lengths to extend the upper platen 150a to different depths in the reservoir 130. Although illustrated as having a substantially cylindrical shape, platens 150 may be formed in various shapes including, but not limited to, rectangularly and other regularly shaped prisms and irregularly shaped prisms.

The lower platen 150b may be secured in place within the reservoir 130 via a screw mount (not illustrated) on the side opposite to the face 220b or may be affixed in the reservoir 130 via an adhesive, welded, brazed or other permanent joint. A screw mount may generally include female threading defined in the body of the lower platen 150b and male threading included in the reservoir 130, or via male threading on a bolt or screw extending from the lower platen 150b to engage with female threading defined in the reservoir 130. A screw mount allows an operator to substitute different lower platens 150b for different tests (e.g., of different materials, thicknesses 210b, designs for the face 220b) or to replace worn platens 150b. An adhesive, welded, or brazed joint permanently secures the lower platen 150b in place, and may be more stable or aid in ease of manufacture compared to a screw mount.

The upper platen 150a may be permanently or temporarily attached to a bracket 230 on a side opposite to the face 220a. In some aspects, the bracket 230 defines one or more through-holes into which a pin 231 can be inserted to define a pivot joint 152 with an axis of rotation orthogonal to the long axis of the cantilever arm 110. In other aspects, the bracket 230 defines a ball joint (or other multi-axis joint) or hinge that defines a pivot joint 152. In some aspects, the bracket 230 defines the platen arm 151 and is connected to the cantilever arm 110 to define a first pivot joint 152a. In other aspects, the bracket 230 engages with a separate platen arm 151 to define a second pivot joint 152b with the pin 231.

The faces 220 of the platens 150 are generally flat surfaces (but for any grooves or tines 240 defined therefrom) that are configured to contact and hold a sample 190 in place during creep testing. Although generally illustrated in the figures as having a greater cross-sectional area than the sample 190, in some aspects the platens 150 have a smaller cross-sectional area than the sample 190. Similarly, although generally illustrated as having equally sized and shaped faces 220 in the figures, the present disclosure contemplates that the first platen 150a and the second platen 150b may have differently sized and/or shaped faces 220a,b from one another.

In various aspects, the faces 220 of the platens 150 (or at least the lower platen 150b) include one or more markers 221 that indicate a distance from a central point of the face 220. The operator can use the markers 221 to align a sample 190 on the center of the face 220 and/or to judge how much or whether the sample 190 has begun to deform under compression. The markers 221 can be formed as grooves cut or etched into the platen 150 or as differently colored gradations on the face 220. In aspects that include several markers 221 at a graduated distance from one another, the markers 221 can define an expansion gauge to measure how much the sample 190 has spread or flowed during creep testing.

The platens 150 can also (optionally) include one or more tines 240 extending from the perimeter and/or the face 220 of the platen 150. The tines 240 extend for a known distance from the faces 220. In various aspects, one or both platens 150 can include tines 240, and one or both platens 150 can exclude tines 240. When beginning the creep testing with a sample 190 of a known height, an operator will know the initial distance between a tine 240 and the face 220 of the opposing platen 150 (e.g., the tines 240 on the second platen 150b are X mm away from the face 220a of the first platen 150a). Accordingly, as the sample 190 deforms under compression, the operator can measure the new distance between various tines 240 and/or the faces 220a,b to determine how much the sample 190 has deformed. Similarly, by measuring this distance at several tines 240 spaced at regular intervals around the sample 190, the operator can determine how evenly the sample 190 is deforming by comparing the change in distances between different tines 240. In some aspects, the tines 240 provide contact points for the sensors 153.

Advantageously, by measuring changes in the distance between the platens 150 (including at known points indicated by the tines 240), a test operator can measure a creep rate of a material without removing the sample 190 from the creep test fixture 100. Accordingly, the measurement of the creep rate can be taken at an intermediate time during creep testing without interrupting the creep testing or touching the sample 190.

Additionally or alternatively, the tines 240 can help capture the sample 190 between the platens 150; preventing the sample 190 from being moved from a central location between the platens 150 due to shear forces and/or uneven compression due to uneven deformation over the course of creep testing.

In various aspects, the tines 240 of the upper and lower platens 150 can be arranged on the respective platens 150 to engage one another or avoid engaging with one another when the platens 150 are in contact. For example, paired tines 240 of the platens 150 may engage one another when the sample 190 is removed from between the platens 150 to prevent the respective faces 220 of the platens 150 from touching. In another example, tines 240 of the platens 150 may engage with the face 220 of the opposing platen 150 to prevent the respective faces 220 of the platens 150 from touching, In other aspects, the tines 240 can be arranged to not engage with the tines 240 or face 220 of the opposing platen 150 (e.g., being defined outside of the perimeter of the opposing platen 150 or with a groove or cavity defined in the body of the opposing platen 150). As illustrated, the tines 240 are substantially cylindrical in shape, but the present disclosure envisions tines 240 having various shapes including, but not limited to, rectangularly and other regularly shaped prisms having flat upper surfaces, or ovoids, pyramids, cones, and other prisms having peaked upper surfaces or points.

Figure 2B:
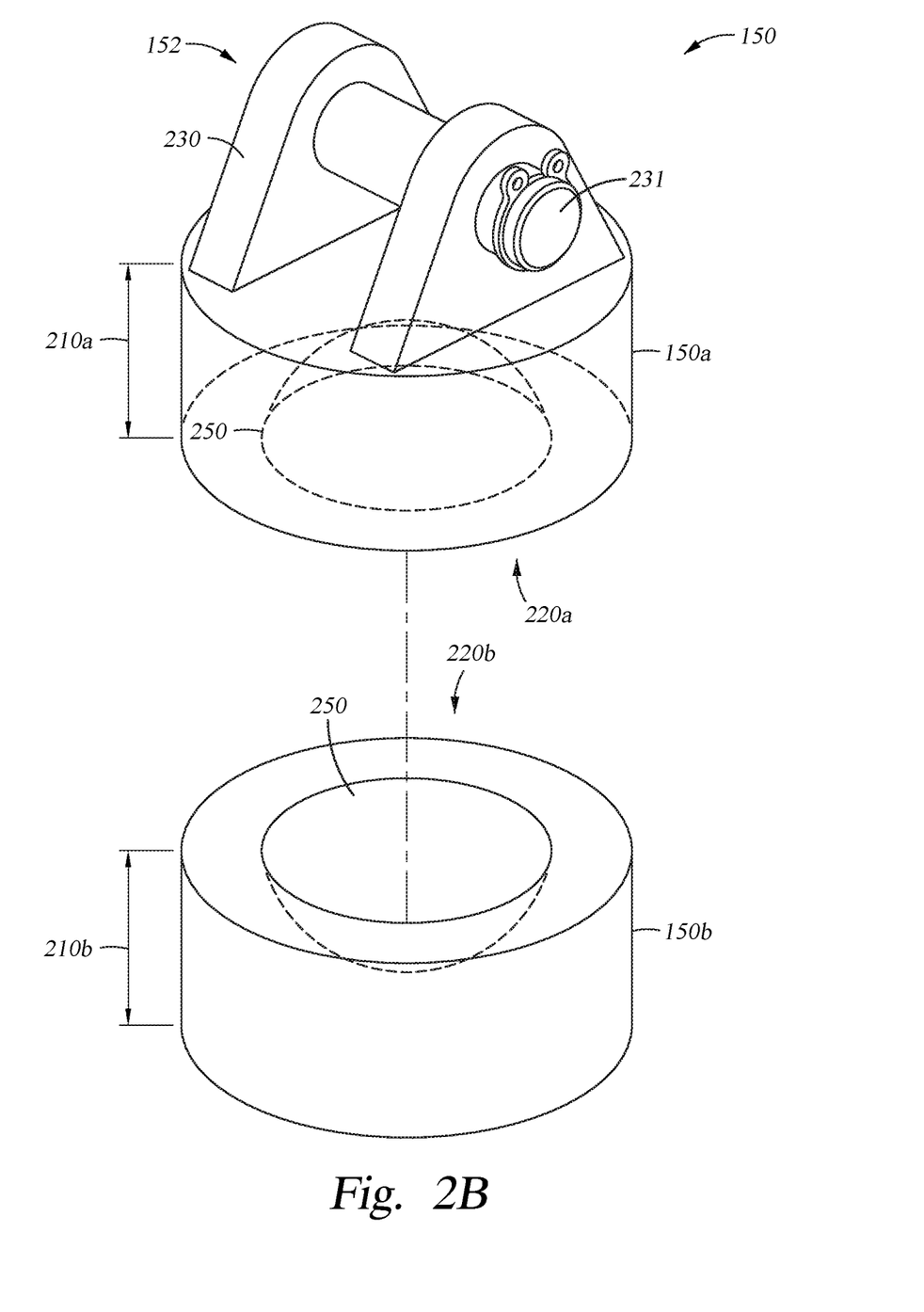

FIG. 2B illustrates detailed views of the platens 150 including cups 250 configured to engage and secure the sample 190, according to aspects of the present disclosure. Similarly to the flat-surfaced platens 150 illustrated in FIG. 2A, the cupped-platens 150 are made of a material that is harder than the sample 190 to be tested and may be provided with various thicknesses 210a,b to set a face 220a,b of the platen 150a,b at various heights relative to the reservoir 130. Additionally or alternatively, the cups 250 can be defined at different depths relative to the faces 220 of the platens 150 to hold different portions of the sample 190 at different heights in the reservoir 130. Although illustrated as having a substantially hemispherical shape (including arc sections less than a full half of a sphere), the cups 250 may be formed in various shapes including, but not limited to, hemicylindrical, rectangularly and other regularly shaped prisms and irregularly shaped prisms.

An operator may freely choose between flat-surfaced platens 150 and cupped platens 150 as shown in FIGS. 2A and 2B, respectively. In some aspects, the upper platen 150a is a first one of a flat-surfaced platen 150 and a cupped platen 150, and the lower platen 150b is a second one of a flat-surfaced platen 150 and a cupped platen 150; allowing the operator to combine both types of platen 150 in a single creep test fixture 100. Similarly, a upper platen 150a and a lower platen 150b that are both cupped platen 150 may define differently shaped cups 250 to accommodate irregularly shaped samples 190. For example, an "ice cream cone" shaped sample 190 may use a lower platen 150b with a conic or pyramidal cup 250 and an upper platen 150a with a semispherical cup 250.

Figure 2C:
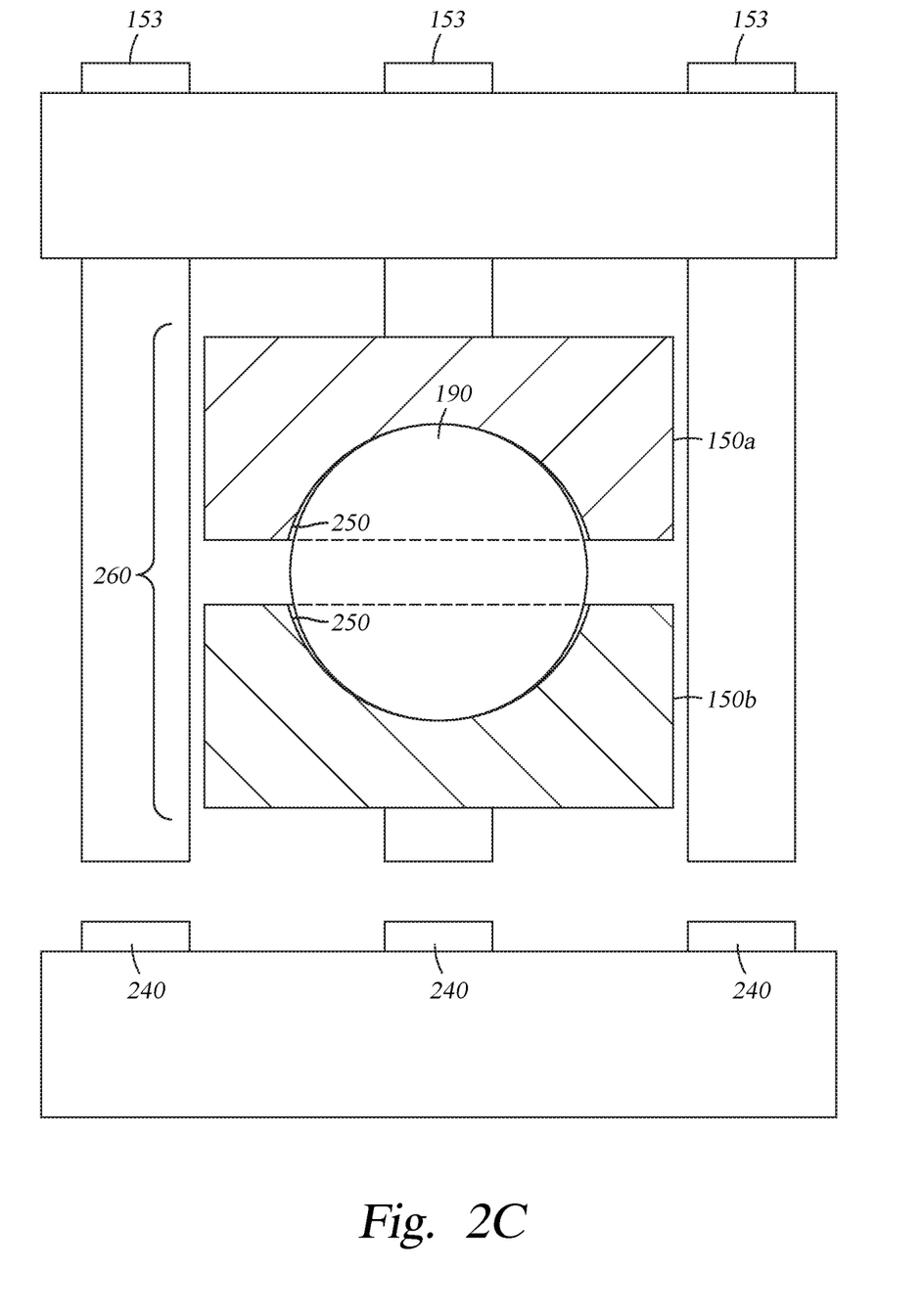
Figure 2D:
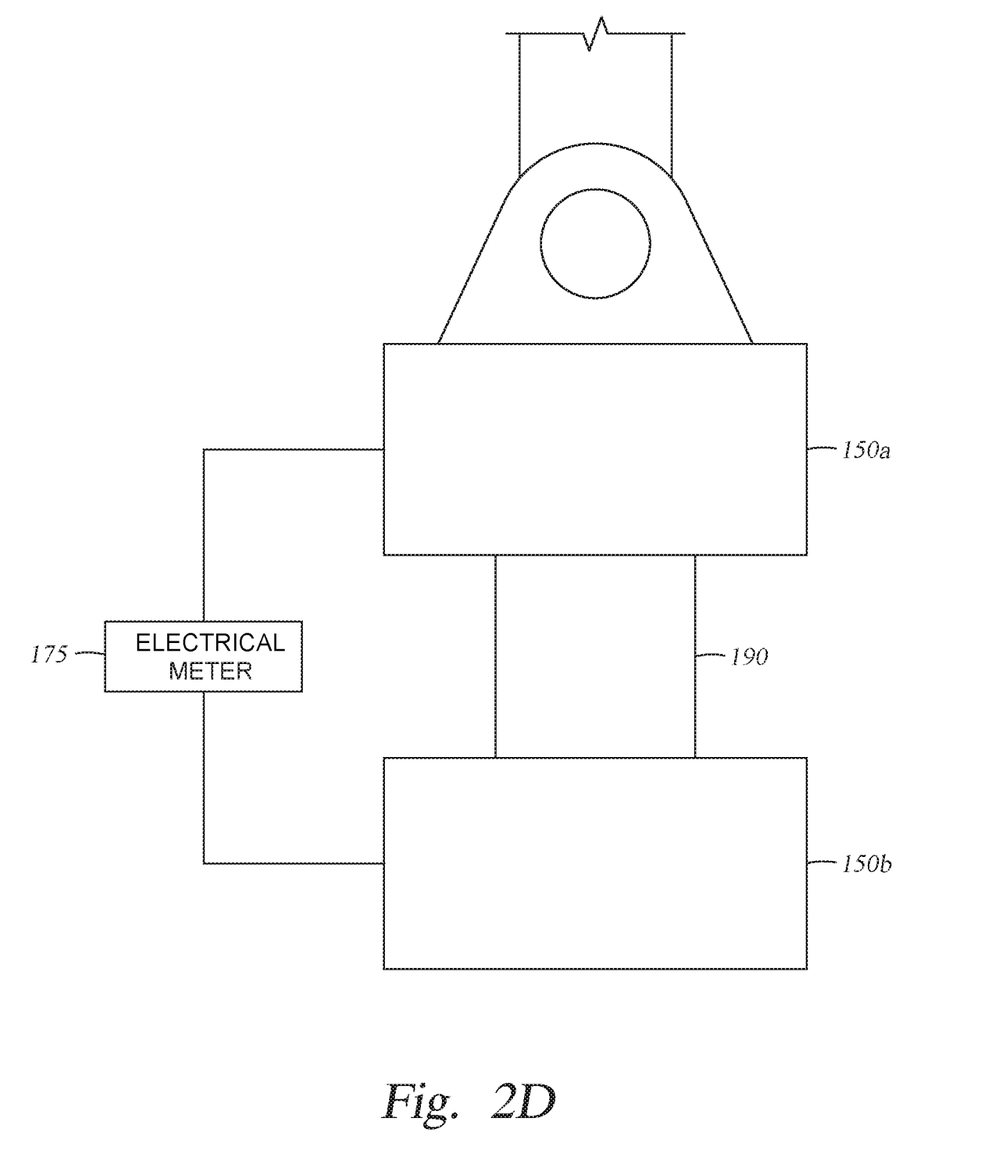

FIG. 2C illustrates a cross-section of two cupped platens 150 capturing a sample 190, according to aspects of the present disclosure. The size and shape of the cups 250 are configured based on the size and shape of the sample 190 to be tested in the creep test fixture 100, and various portions of the sample 190 may protrude from the cups 250. When one or more of the cups 250 are defined by a curved surface (e.g., as with a generally hemispherical or hemicylindrical cross-section), the cups 250 and sample 190 interact to provide a self-aligning joint 260 to account for any material deformation in the sample 190 during creep testing. Although not illustrated, the platens 150 may also include various connection points for compressive springs or clips that can help secure the sample 190 between the platens.

Figure 3:
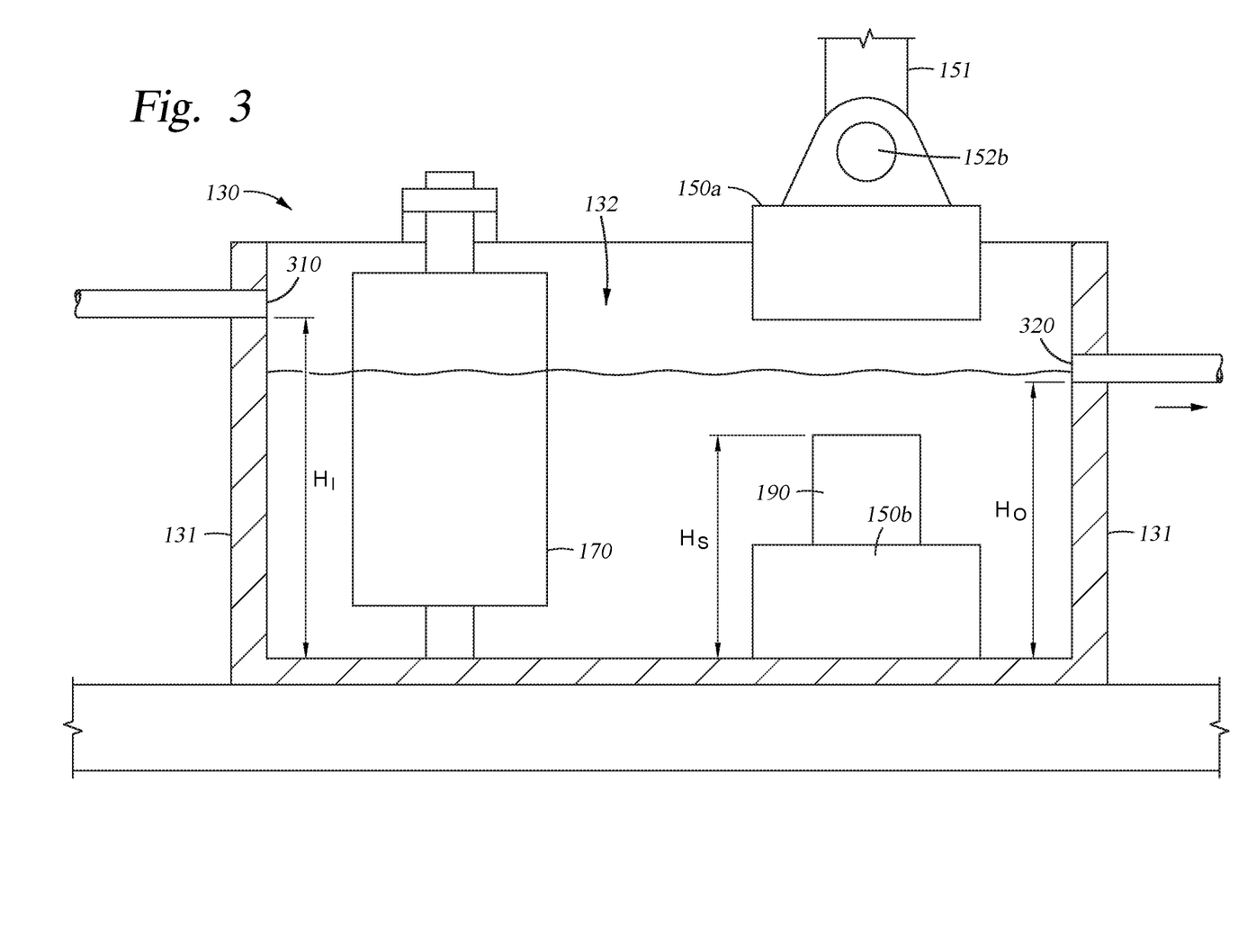
FIG. 3 illustrates a cutaway view of the reservoir, according to aspects of the present disclosure.

FIG. 3 illustrates a cutaway view of the reservoir 130, according to aspects of the present disclosure. The reservoir 130 is designed to hold a fluid in which the sample 190 is submerged during creep testing. In various aspects, the fluid can be water (deionized, doped with specific ions, sea water, drinking water, etc.), alcohol, a lubricant (e.g., various types of oils), a coolant or refrigerant (e.g., liquid nitrogen, Freon), a fuel or propellant (e.g., jet fuel, gasoline, kerosene, liquid oxygen), hydraulic fluids, mixtures thereof and other fluids of interest.

The walls 131 provide a fluid barrier to contain a fluid in which the sample 190 is (fully or partially) submerged during creep testing. A floor or bottom surface of the reservoir 130 can optionally be provided by a surface of the base 180 to which the walls 131 are attached, or by a dedicated wall on the underside of the reservoir 130. The walls 131 are provided of a height greater than that of the combined height of the second platen 150b the sample 190 (when included) so that a fluid held in the fluid basin 132 can submerge the sample 190 (i.e., the fluid level covers at least a desired portion of the sample 190 in the fluid).

A fluid inlet 310 is defined at a first or inlet height (Hi) in the reservoir 130, which is at or above the height (Hs) at which the upper surface of the sample 190 rests. The fluid inlet 310 is configured to allow fluid to flow into the fluid basin 132 from an external source (e.g., via one or more pumps and associated pipes from a fluid tank, the fluid outlet 320 of a second reservoir 130 associated with a different creep test fixture 100). In various aspects, the flow of the fluid may be constant, may be reactive (e.g., in response to the fluid level dropping below a threshold) or may be periodic (e.g., X mL are deposited once a day).

A fluid outlet 320 is disposed at a second or outlet height (Ho) in the reservoir, which can be at or above the height (Hs) at which the upper surface of the sample 190 rests or at or below the height at which the sample 190 rests when the fluid inlet 310 provides a constant flow of fluid into the reservoir. In various aspects, the fluid outlet 320 is positioned at the same height as the fluid inlet 310, below the height of the fluid inlet 310, or above the height of the fluid inlet 310 (e.g., as an overflow outlet). The fluid outlet 320 is configured to allow fluid to flow out of the fluid basin 132 and may be linked (via one or more pipes) to a fluid disposal tank, a recycling filter for the external source, the reservoir 130 of a different creep test fixture 100, or the like.

In various aspects, multiple fluid outlets 320 are provided at different heights for different purposes, and one or more of the fluid outlets 320 may be selectively disabled (i.e., preventing flow). For example, a first fluid outlet 320 may be located at the bottom of the reservoir 130 as a drain that is blocked or disabled during creep testing, but opened at the conclusion of creep testing to remove the fluid from the reservoir 130. Continuing the example, a second fluid outlet 320 may be located at or near the top of the reservoir 130 as an overflow outlet to protect against spillage of the fluid outside of the reservoir 130 in the event of excess fluid being added to the reservoir 130.

In some aspects, the fluid outlet 320 is located at a position in the reservoir 130 relative to the fluid inlet 310 to ensure that the fluid flows over the sample 190. For example, the fluid inlet 310 and the fluid outlet 320 are located on opposite sides of the reservoir 130 relative to the sample 190. In other aspects, the fluid outlet 320 is located at a position in the reservoir 130 relative to the fluid inlet 310 to ensure that the fluid is substantially stagnant over the sample 190. For example, the fluid inlet 310 and the fluid outlet 320 are located next to one another to maintain a fluid level above the upper surface of the sample 190 and below a maximum height of the walls 131 of the reservoir 130 that minimized movement of the fluid within the fluid basin 132 while maintaining a desired fluid level.

Figure 4:
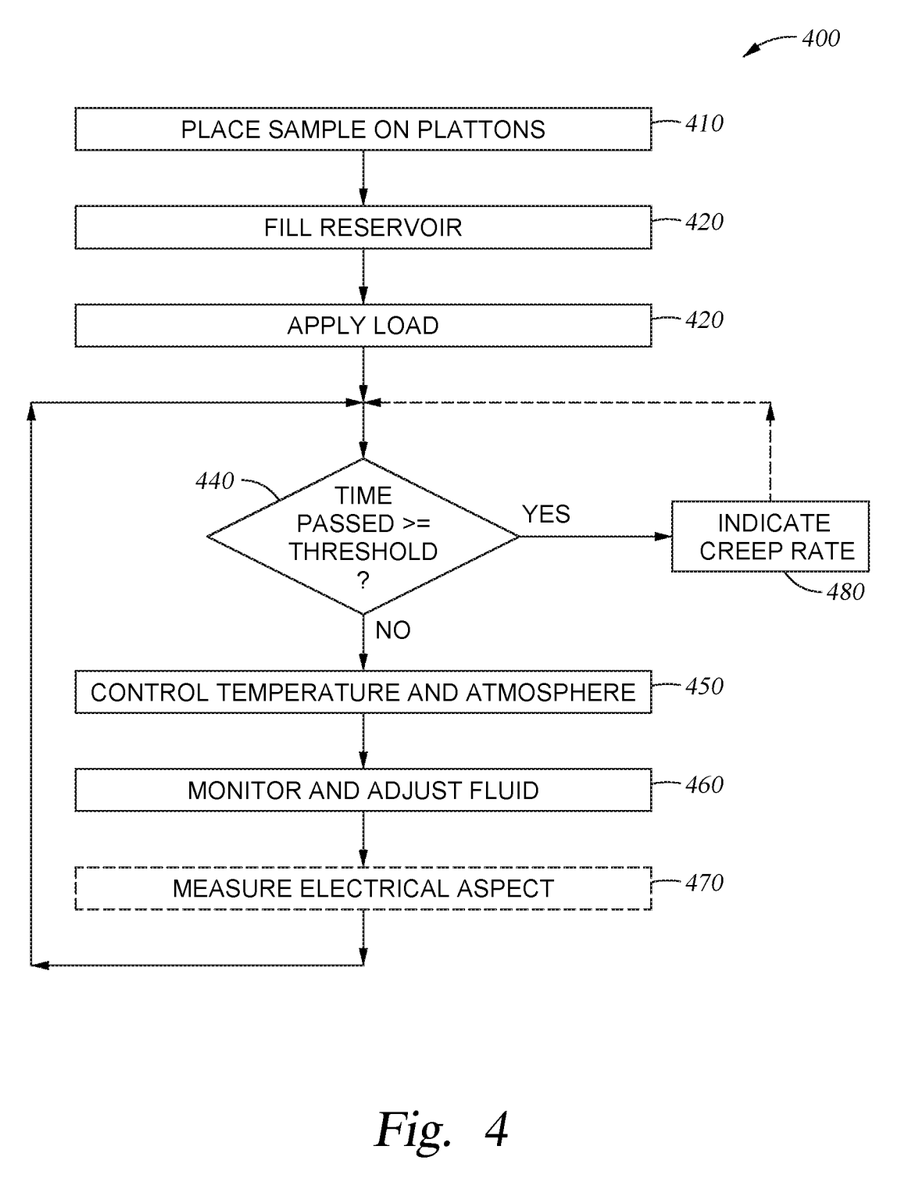
FIG. 4 is a flowchart of a method for creep testing a sample using the creep test fixture, according to aspects of the present disclosure.

FIG. 4 is a flowchart of a method 400 for creep testing a sample 190 using the creep test fixture 100, according to aspects of the present disclosure. Method 400 may be performed in parallel using several creep test fixtures 100 using the same or different samples 190 and the same or different weights 140 in a shared environment. For example, one or several creep test fixtures 100 may be placed in a controlled environmental chamber for up to a predefined length of time to measure the creep of a material under similar conditions.

Method 400 begins with block 410, where a sample 190 is placed on a lower platen 150b of the creep test fixture 100. In various aspects, the sample 190 is a predefined size and shape of a material to place under creep testing, which the test operator places on the center of the lower platen 150b in a desired orientation (e.g., positioning the material grain in a desired orientation, placing the indicated top upward, etc.). The lower platen 150b can include various alignment features, such as, for example, tines 240 or markers 221 enable the test operator to accurately position the sample 190 on the face 220 of the lower platen 150b. The test operator then closes the creep test fixture 100 to secure the sample 190 between the lower platen 150b and the upper platen 150a.

At block 420, the test operator fills the reservoir 130 with the fluid in which the sample 190 is to be compressed and sets the environmental conditions for use during creep test. In various aspects, the fluid fills the reservoir via a fluid inlet 310, while in other aspects, the test operator may fill the reservoir 130 by pouring the fluid into the reservoir 130. The fluid fills the reservoir 130 to a level that submerges the sample 190. In various aspects, the order of blocks 410 and 420 may be reversed or block 410 can be repeated after block 420 to adjust where the sample 190 is located after the fluid has filled the reservoir 130 to a desired fluid level. The test operator also sets the environmental conditions for use during creep testing, which can include activating temperature and atmospheric controllers to maintain a test environment of chamber within a predefined temperature range and/or atmospheric pressure and/or composition. As will be appreciated, the creep test fixture 100 can be used without a liquid in the reservoir 130 (e.g., using a gaseous fluid or vacuum) and block 420 may be performed by setting a test chamber in which the creep test fixture 100 is held to a predefined atmosphere and temperature.

At block 430, the test operator applies the compressive load to the sample 190. The test operator selects an appropriate number of weights 140 to secure to the cantilever arm 110 to impart a desired compressive force between the platens 150 to the sample 190. The test operator considers the mechanical advantage of the cantilever arm 110 (based on the relative distances of where the weights 140 are applied and the swivels on the cantilever arm 110 are located) to select the amount of weights 140 to secure to the weight holder 111 to thereby impart the desired compressive force. Once the appropriate number of weights 140 are secured, the test operator places the upper platen 150a in contact with the sample 190, and allows the compressive force to be transferred between the platens 150 and the sample 190 (e.g., by disengaging a compression interlock 160, lowering the cantilever arm 110, etc.).

At block 440, the test operator determines if the amount of time since applying the compressive load to the sample 190 (per block 430) satisfies a threshold amount of time. In various aspects, the threshold amount of time can be the predefined amount of time to perform creep testing or may be a milestone or intermediate time during creep testing at which an intermediate measurement of creep rate is to be taken. When the amount of time passed does not satisfy the threshold, method 400 proceeds through blocks 450-470 before returning to block 440 for a subsequent determination at a later time. Otherwise, when the amount of time passed satisfies the threshold, method 400 proceeds to block 480, where method 400 may optionally conclude or return to block 440 for a subsequent determination at a later time. In various aspects, method 400 also proceeds to block 450-470 when proceeding to block 480; blocks 440-470 may be performed constantly during creep testing and independently of whether block 480 is performed.

At block 450, the test operator controls the temperature and atmosphere in which the creep test fixture 100 is disposed. For example, a test environment may be maintained in a test chamber at a known temperature range with a known gas composition (e.g., X % humidity air, argon, nitrogen) at a predefined pressure (e.g., standard sea level pressure, cruising cabin pressure for an aircraft, operational pressures for a component). The test chamber can accommodate one or more creep test fixture 100 at a time, thus allowing the test operator to perform several creep tests in parallel with similar temperature and atmospheric conditions.

At block 460, the test operator monitors and adjusts the fluid in the reservoir 130. The test operator monitors and adjusts the fluid level in the reservoir 130 by adjusting the rates at which the fluid enters and/or exits the reservoir 130 to keep the sample 190 submerged to replace losses due to evaporation, wicking, or outflow. In various aspects, the positioning of the fluid inlet 310 and outlet 320 and the time(s) and rate at which fluid is added to the reservoir ensure that the sample 190 remains submerged. Additionally or alternative, the test operator monitors and adjusts the temperature of the fluid either in the reservoir 130 or in the fluid source to maintain the fluid at a desired temperature.

At block 470, the test operator (optionally) measures an electrical aspect of the sample 190. In various aspects, the test operator measures one or more of: resistance, conductivity, impedance, voltage breakdown, etc., in alternating current AC or DC scenarios. The electrical meter 175 is configured to account for the sample 190 being fully or partially submerged in a fluid, and the effects of the fluid on the measured electrical aspect. The electrical meter 175 measures the values of the electrical aspect(s) over time to determine the effects of the fluid and creep on the material of the sample 190, and may record values measured at a rate to collect a plurality of values over the life of the creep test.

At block 480, the test operator measures a creep rate of the sample 190 at the length of time that has passed since the load was applied to the sample 190. In various aspects, to indicate the creep rate of the given material of the sample 190 in the presence of the given fluid used to fill the reservoir 130 (per block 420), the test operator measures the height and the cross-sectional area of the sample 190. In various aspects, the test operator measures the distances between the faces 220 of the platens 150 (and any changes therein from the initial distance based on the initial height of the sample 190) and/or the tines 240 of the platens 150 to help identify the height of the sample 190 without removing the compressive force from the sample 190. In some aspects, the test operator measures the spread of the sample 190 over one or more markers 221 on the face 220 of the platen 150 to identify the cross-sectional area of the sample 190 without removing the compressive force from the sample 190. Method 400 may conclude at block 480 when the length of time passed corresponds to the predefined amount of time for creep testing, but otherwise returns to block 440 for additional monitoring.

In the current disclosure, reference is made to various aspects. However, it should be understood that the present disclosure is not limited to specific described aspects. Instead, any combination of the following features and elements, whether related to different aspects or not, is contemplated to implement and practice the teachings provided herein. Additionally, when elements of the aspects are described in the form of "at least one of A and B," it will be understood that aspects including element A exclusively, including element B exclusively, and including element A and B are each contemplated. Furthermore, although some aspects may achieve advantages over other possible solutions and/or over the prior art, whether or not a particular advantage is achieved by a given aspect is not limiting of the present disclosure. Thus, the aspects, features, aspects and advantages disclosed herein are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects described herein may be embodied as a system, method or computer program product. Accordingly, aspects may take the form of an entirely hardware aspect, an entirely software aspect (including firmware, resident software, micro-code, etc.) or an aspect combining software and hardware aspects that may all generally be referred to herein as a "circuit," "module" or "system." Furthermore, aspects described herein may take the form of a computer program product embodied in one or more computer readable storage medium(s) having computer readable program code embodied thereon.

Program code embodied on a computer readable storage medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatuses (systems), and computer program products according to aspects of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block(s) of the flowchart illustrations and/or block diagrams.

These computer program instructions may also be stored in a computer readable medium that can direct a computer, other programmable data processing apparatus, or other device to function in a particular manner, such that the instructions stored in the computer readable medium produce an article of manufacture including instructions which implement the function/act specified in the block(s) of the flowchart illustrations and/or block diagrams.

The computer program instructions may also be loaded onto a computer, other programmable data processing apparatus, or other device to cause a series of operational steps to be performed on the computer, other programmable apparatus or other device to produce a computer implemented process such that the instructions which execute on the computer, other programmable data processing apparatus, or other device provide processes for implementing the functions/acts specified in the block(s) of the flowchart illustrations and/or block diagrams.

The flowchart illustrations and block diagrams in the Figures illustrate the architecture, functionality, and operation of possible implementations of systems, methods, and computer program products according to various aspects of the present disclosure. In this regard, each block in the flowchart illustrations or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order or out of order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

While the foregoing is directed to aspects of the present disclosure, other and further aspects of the disclosure may be devised without departing from the basic scope thereof, and the scope thereof is determined by the claims that follow.

What is claimed is:

1. An apparatus, comprising:
    a cantilever arm connected on a first end to a cantilever pivot and including a weight holder on a second end;
    a first platen connected to the cantilever arm via a swivel located between the first end and the second end;
    a reservoir; and
    a second platen disposed within the reservoir and positioned to secure a sample between the first platen and the second platen when a force is applied via the weight holder and the first platen to a sample.

2. The apparatus of claim 1, further comprising:
    a compression interlock configured to position the second end of the cantilever arm at one of a first height and a second height, wherein:
        at the first height the first platen is positioned to transfer the force applied via the weight holder to a sample positioned on the second platen, and
        at the second height the first platen is positioned to not transfer the force applied via the weight holder to a sample positioned on the second platen.

3. The apparatus of claim 1, wherein the first platen and the second platen respectively define a first flat surface and a second flat surface configured to contact a sample of a smaller cross-sectional area than the first platen or the second platen.

4. The apparatus of claim 3, wherein at least one of the first platen or the second platen includes an expansion gauge.

5. The apparatus of claim 1, wherein the reservoir further comprises:
a fluid basin in which the second platen is disposed, wherein the fluid basin extends to a first height greater than a height of a sample held between the first platen and the second platen;
a fluid inlet disposed at a second height at or above the first height, wherein the fluid inlet is configured to configured to allow fluid to flow into the fluid basin; and
a fluid outlet disposed at a third height at or above the first height and at or below the second height, wherein the fluid outlet is configured to allow fluid to flow out of the fluid basin.

6. The apparatus of claim 1, wherein the swivel is configured to keep the first platen in contact with a sample held between the first platen and the second platen as the sample deforms under the force applied via the weight holder and the first platen.

7. The apparatus of claim 1, further comprising:
an electrical meter defined in the reservoir, configured to measure an electrical aspect of the sample held between the first platen and the second platen while the first platen is electrically isolated from the second platen.

8. A device, comprising:
a reservoir including a fluid basin in which a first platen, a sample positioned on the first platen, and a fluid rising to a fluid level above an upper surface of the sample are included;
a cantilever including:
a mount mounted to a surface on which the reservoir is disposed and including a pivot;
a cantilever arm connected on a first end to the pivot including a weight holder on a second end opposite to the first end and including a swivel between the first end and the second end; and
a second platen connected to the swivel and held in contact with the upper surface of the sample via a downward force applied on the second end to transfer a compressive load to the sample.

9. The device of claim 8, wherein the fluid is one of deionized water, jet fuel, and hydraulic fluid.

10. The device of claim 8, wherein the sample is made of a polymer material with a lower hardness than the first platen and the second platen.

11. The device of claim 8, further comprising: an electrical meter disposed in the reservoir and configured to measure an electrical aspect across the sample.

12. The device of claim 8, further comprising a fluid level sensor configured to generate an alert when a fluid level is at or below the upper surface of the sample.

13. The device of claim 8, wherein the reservoir further comprises:
a fluid inlet configured to deposit fluid into the reservoir; and
a fluid outlet configured to remove fluid from the reservoir, wherein the fluid outlet is disposed at an outlet height above the upper surface of the sample.

14. The device of claim 8, further comprising a test chamber configured to control a temperature of an environment in which the reservoir is disposed.

15. The device of claim 8, wherein the weight holder comprises a dowel configured to receive and hold in position one or more weights of one or more predefined weights.

16. The device of claim 15, wherein the one or more weights held by the weight holder are selected based on a length of the cantilever arm, a distance between the pivot and the second end, and a desired level of the compressive load to apply.

17. A method, comprising:
placing a sample of a given material between a first platen and a second platen, wherein:
a cross-sectional area of the first platen and a cross-sectional area of the second platen is greater than a cross-sectional area of the sample, and
the sample is a disposed in a reservoir;
filling the reservoir with a fluid to submerge the sample within the reservoir;
applying a load to a cantilever arm connected to the first platen to impart a compressive force between the first platen and the second platen to the sample;
in response to a predefined length of time passing, measuring a second height and a second cross-sectional area of the sample; and
indicating a creep rate of the given material in presence of the fluid.

18. The method of claim 17, further comprising:
measuring a force between the cantilever arm and the first platen.

19. The method of claim 17, further comprising:
monitoring a level of the fluid over the predefined length of time; and
in response to the level of the fluid dropping to a predefined level, adding additional fluid to the reservoir to keep the sample submerged.

20. The method of claim 17, further comprising: measuring an electrical aspect of the sample between the first platen and the second platen.

* * * * *